US006547824B1

(12) United States Patent
Price

(10) Patent No.: US 6,547,824 B1
(45) Date of Patent: *Apr. 15, 2003

(54) EXTENDED LIFE PROSTHETIC JOINTS THROUGH THERMAL MANAGEMENT

(76) Inventor: Peter E. Price, 20 Johnson Rd., Andover, MA (US) 01810

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/382,548

(22) Filed: Aug. 25, 1999

Related U.S. Application Data
(60) Provisional application No. 60/133,755, filed on May 12, 1999, and provisional application No. 60/097,823, filed on Aug. 25, 1998.

(51) Int. Cl.$^7$ .............................. A61F 2/30; A61F 2/36
(52) U.S. Cl. .................. 623/18.11; 623/23.11
(58) Field of Search ................ 623/23.11, 22.21, 623/18.11

(56) References Cited

U.S. PATENT DOCUMENTS

| | | | |
|---|---|---|---|
| 4,263,681 A | 4/1981 | Notton | 3/1.91 |
| 4,535,486 A | 8/1985 | Roberts et al. | 623/22 |
| 4,547,910 A | 10/1985 | Roberts et al. | 623/18 |
| 4,743,308 A | * 5/1988 | Sioshansi et al. | 148/4 |
| 5,152,794 A | 10/1992 | Davidson | 623/16 |
| 5,593,719 A | 1/1997 | Dearnaley et al. | 427/2.26 |

OTHER PUBLICATIONS

Davidson et al., "Wear, creep, and frictional heat of femoral implant articulating surfaces and the effect on long–term performance–Part I, A review" J. Biomed. Mater. Res.: Applied Biomaterials vol. 21, No. A3, 1987, pp. 261–285.

Davidson et al., "Wear, creep, and frictional heating of femoral implant articulating surfaces and the effect on long–term performance–Part II, Friction, heating, and torque" J. Biomed. Mater. Res.: Applied Biomaterials, vol. 22, No. A1, 1988, pp. 69–91.

Lu et al., "Frictional heating of bearing materials tested in a hip joint wear simulator" Proc Instn Mech Engrs, vol. 211 Part H, 1996, pp. 101–108.

Lewis, "Polyethylene Wear in Total Hip and Knee Arthroplasties" Journal of Biomedical Materials, vol. 38, Issue I, 1997, pp. 55–75.

Lu et al., "Potential Thermal Artifacts In Hip Joint Wear Simulators" Transactions, vol. 23 Sec. 1, 1998, p. 358.

Tai–Horng Young et al., "Analysis of Ultrahigh Molecular Weight Polyethylene Failure in Artificial Knee Joints: Thermal Effect on Long–Term Performance" Journal of Biomedical Materials, vol. 48, Issue 2, 1999, pp. 159–164.

Klein et al., "Effect of Contact Stress and Other Variables on UHMWPE Friction/Wear in Total Hip Replacement" Transactions, vol. XXII, 1999, pp. 179.

Salehi et al., "Effect of Head Material And Size; Serum Concentration, Recirculation, and Temperature; Cyclic Frequency; And Load Magnitude On Head/Liner Temperatures In An Anatomical Hip Wear Simulator" Transactions, vol. 23 Sec. 1, 1999, p. 53.

Duus et al., "The Role of Polyethylene Lamellar Size In Material Properties" Transactions, vol. 23 Sec. 1, 1999, p. 841.

\* cited by examiner

Primary Examiner—Bruce Snow
(74) Attorney, Agent, or Firm—Herbert A. Newborn

(57) ABSTRACT

A prosthetic joint in an embodiment has two load-bearing surfaces that are slidingly disposed relative to each other and define a region of frictional contact. The joint is thermally managed as heat is removed from the region during joint use by thermal conduction so that the surfaces are maintained approximately at or below specified temperatures. In other embodiments, heat flows preferentially through one member which includes one of the surfaces. Use of high thermal conductivity materials in conjunction with various joint designs affording thermally managed devices are provided in numerous embodiments.

11 Claims, 7 Drawing Sheets

EXTENDED LIFE PROSTHETIC JOINTS THROUGH THERMAL MANAGEMENT

RELATED U.S. APPLICATIONS

The present application claims priority from Provisional Application Serial No. 60/097,823 filed on Aug. 25, 1998, and from Provisional Application Serial No. 60/133,755, filed May 12, 1999, both of which are hereby incorporated herein by reference.

TECHNICAL FIELD

The present invention relates to artificial joints, including those for use in hip and knee replacements.

BACKGROUND ART

There is a growing need for extension of the useful life of man-made prosthetic joints. For example, total hip replacement surgeries have been performed in the United States since 1971 with many hundreds of thousands of patients receiving needed artificial joints. Many of these installations have failed and have required more complicated and costly revisions or repairs. Many of the currently installed devices including hips and knees are expected to have a useful life of only 10–15 years depending on many factors including the level of activity of the recipients. A major factor contributing to these failures is the wear of one of the mated load-bearing surfaces which is most commonly and traditionally made from ultra-high molecular weight polyethylene (UHMWPE), a polymer with a microstructure having a crystalline phase material (usually present in the range of about 40 to 80% by volume) embedded in a noncrystalline phase matrix. Wear of this material results in loss of the original functionally engineered geometrically designed contours of artificial hips, namely, the wearing of a deep socket in the UHMWPE cup and related production of nanoscale particulate polymer wear debris. The debris, in turn, triggers an adverse foreign body response in the region of the installed device. This in vivo response can produce collateral damage leading to loosening of members of the device, subsequent dysfunction and pain and, ultimately, the need for surgical repair or revision.

Corrosion-resistant metal alloys and, less often, ceramics are used for the ball member of a hip joint which replaces the original anatomical femoral head. UHMWPE is the current material of choice for the cup member which replaces the surface of the pelvic opening known as the acetabulum. A great deal of research has been performed to find suitable and improved ball materials from the standpoint of reducing friction and wear against UHMWPE while assuring corrosion resistance and overall biocompatibility. These efforts carried out over the last 15–20 years have resulted in a short list of commonly accepted ball and stem materials for artificial hips and other prosthetic applications. This list includes AISI 316 stainless steels, cast cobalt-chromium-molybenum alloys, wrought cobalt-chromium alloys, unalloyed titanium, Ti-6Al-4V alloys, and cobalt-chromium-nickel alloys. Additionally, these alloys have been modified using various surface treatments for improved properties relative to prosthetic applications.

Another area of intense research on prosthetic materials has recently focused on improving the UHMWPE material used as a load bearing material opposing the metal or ceramic component of these artificial joint devices. This research has produced a variety of chemical and thermal processing methods which, taken in combination, alter the structure of the polymer. This structure-altered material is characterized in part by a reduction in scale and size of the crystalline phase lamellae within the microstructure as compared to the scale and size of lamellae in non-altered material.

Today, the cobalt-chromium-molybdenum alloys known under the standardization identity of ASTM F-75 and derivative identities are used most extensively for the ball material. ASTM F-75 type alloys contain up to 0.36 wt % carbon. This is primarily for the historical reason related to the adaptation and standardization of an alloy suitable for prosthetic applications from a cobalt-base, high temperature superalloy known to have corrosion resistance significantly exceeding that of stainless steel. This adaptation of the Haynes Stellite (HS-21), otherwise known as Modified Vitallium alloy, occurred at a time preceding the current more complete understanding of the mechanisms governing wear in prosthetic devices. There is a further historical relationship in the current use of this alloy as a prosthetic material in that the original composition developed by the Austenal Company was developed and used as a prosthodontic alloy in the late 1930's. As is known in the metallurgical art, the simultaneous presence of carbon and chromium in a cobalt based alloy will result in the presence of hard phase chromium carbides dispersed within grains and at grain boundaries. Such a dispersion may be non uniform in cast structures with concentrations of carbides at grain boundaries. Because of the high atomic ratio of chromium to carbon in high chromium alloys, these carbides ($Cr_{23}C_6$) are more resistant to corrosion than the surrounding matrix. In the current art, it is known that in vivo corrosion of these cobalt alloys does take place as evidenced by recovery of metal ions in tissues and fluids surrounding installed prosthetic devices, and these carbides will, in time, end up in positive relief as asperities. Such asperities are believed to contribute to a ploughing effect in the accelerated wear of a matching UHMWPE cup surface of a prosthetic joint device. These carbides may also end up in relief in the manufacturing process because they inherently resist the polishing process used to produce the final surface finish of the femoral ball.

The evolutionary development of prosthodontic materials has resulted today in the availability of a wide range of noble metal alloys containing gold, platinum, palladium, silver, and small amounts of other elements used for control of processing, structure, and properties. These alloys have been proven to be corrosion resistant and biocompatible over long periods of time. In addition, they can be formulated and processed to produce hardness sufficient to withstand use in two body and three body friction and wear processes, in the chewing of food including hard foods and foods containing exogenous particles of very hard grit or foreign substances, such that the useful life of installed devices constructed from these noble metal alloys frequently exceeds 30 years or more. A unique characteristic related to these noble metal alloys is that they are not chemically capable of forming hard phases such as carbides, nitrides and oxynitrides as is well known in the metallurgical art and documented in the phase diagram literature. Thus, ploughing effects in wear produced by particles of this nature standing in microscopic relief do not occur with use of such noble metal alloys.

In the literature of the art on friction and wear (Friction and Wear of Materials, Rabinowitz, Wiley 1965), a quantitative law of adhesive wear (i.e. wear in the absence of third body abrasive particles) is given by the Holm equation (Holm, 1946). The worn-away volume, V, is stated as:

$$V = K \times W \times L / H,$$

where:
- K is a constant depending on materials in contact and the extent of surface modification by lubricants, fluids, or other adsorbed chemical species,
- W is the load,
- L is the total sliding distance (for prosthetic devices in effect the useful life of the component most susceptible to wear, and
- H is the hardness of the softer of the pair of materials in contact.

The hardness of the softer UHMWPE has certain published values taken at room temperature, most commonly 293° K. This polymer is a crystalline polymer with a volume fraction of crystalline material ranging from about 40 to 80% depending on its thermal processing history. In vivo, this polymer operates at 310° K when it is at equilibrium with its surroundings. The nominal crystalline melting point ($T_{mp}$) of this polymer is 410° K. On an absolute temperature scale, the operating (or homologous) temperature of 310° K is 0.76 $T_{mp}$ or higher. In the field of materials science of crystalline solids, most commonly metals and ceramics, operation at a homologous temperature of 0.76 constitutes a high temperature use requiring appropriate temperature related design rules. UHMWPE is a low temperature material being applied in a high temperature regime when used in prosthetic devices.

In addition to the quantitative law of adhesive wear referred to above, an area of extreme interest to the early workers in the field of friction and lubrication of solids was the surface temperature produced during frictional rubbing of various pairs of materials, most commonly metals (Bowden and Tabor, The Friction and Lubrication of Solids, Oxford 1950). When one solid body slides over another, a significant portion of the mechanical work done against friction for devices where the coefficient is greater than zero is liberated as heat generated at or near the sliding surfaces. In artificial prosthetic joints installed in users (i.e. in vivo), this heat is dissipated by thermal conduction into the biological surroundings having a base reference temperature of 310° K. Following known laws of heat transfer, the rate of thermal conduction of this frictional heat is controlled by a series of thermal resistances characterized by: 1. the dimensions and thermal conductivities of the materials of construction of the device, 2. the thermal contact resistances within the device in the cases of multipart or modular devices, 3. the thermal conductivities and thicknesses of cements or other substances used for device fixation, 4. the dimensions and thermal conductivity of bone into which the device is mounted or embedded, and 5. the thermal resistance or heat transfer film coefficients from bone and directly exposed device materials to the surrounding fluids and tissues around the device where such surroundings are fixed at an environmental temperature of 310° K.

SUMMARY OF THE INVENTION

Embodiments of the present invention solve problems of the prior art with respect to maintaining load-bearing surfaces of prosthetic joints approximately at or below specified temperatures. Such thermal management solutions may yield extended life joints. Accordingly, in a first embodiment of the invention, a prosthetic joint includes a first member, with a first load-bearing surface and a second member, with a second load-bearing surface. The surfaces are slidingly disposed relative to each other defining a region of frictional contact during joint use. Heat is removed from the region during joint use by thermal conduction through at least one of the first and second members so that the first and second surfaces are maintained approximately at or below a specified temperature. The specified temperature may be less than a lowest melting point of a material of either of the surfaces. Alternatively, the specified temperature may be less than a temperature that destroys organic species indigenous to an in vivo joint. Also, the specified temperature may be equal to about that of surroundings in which the joint is used. The specified temperature may be equal to about 310° K.

Thermal conduction may occur through the first member which may further have a first load-bearing portion that includes the first surface and a first body portion that is bonded to the first load-bearing portion. In another embodiment, the first member has greater than about seventy-five times higher conductivity than the second member when the conductivities are measured at about 310° K. The first load-bearing portion may have a thermal conductivity higher than about 30 W/m° K. The second member may contain polymeric material and may further have a second load-bearing portion that includes the second surface and a second body portion that is coupled to the second load-bearing portion. The polymeric material may be ultra-high molecular weight polyethylene and may have a thermal conductivity of less than about 0.4 W/m° K. The prosthetic joint may serve as an artificial hip wherein the first member is ball-shaped and the second surface of the second member is cup-shaped and is sized to mate with the first member. In another embodiment, the second member may be ball-shaped and the first surface of the first member is cup-shaped and is sized to mate with the second member. The joint may also serve as an artificial knee.

In yet another embodiment, the first body portion also has a heat pipe core and a biocompatible casing surrounding the heat pipe core. The heat pipe core may have a thermal conductivity of greater than about 50 W/m° K.

In a further embodiment, the first member also has a first load-bearing portion that includes the first surface, a first support portion that is bonded to the first load-bearing portion, and a stem that is mechanically coupled to the first support portion. The first support portion may further serve as a heat pipe in conducting heat from the first surface and may have a thermal conductivity of greater than about 50 W/m° K. The stem may further have a heat pipe core and a biocompatible casing surrounding the heat pipe core. The biocompatible casing may be constructed from the same material as is the first-load bearing surface.

In another embodiment, the specified temperature may be less than a temperature at which the Meyer hardness of polyethylene decreases to about ninety percent of its Meyer hardness measured at about 310° K. The first member may contain gold.

In yet another embodiment, a prosthetic joint has a first load-bearing surface, a second load-bearing surface, the surfaces slidingly disposed relative to each other defining a region of frictional contact, and a heat pipe coupled to at least one of the first and second surfaces. Heat is conducted via the heat pipe from the region to surroundings during joint use; the heat pipe having a thermal conductivity of greater than about 50 W/m° K. One of the first and second load-bearing surfaces may contain gold. The heat pipe may be constructed from material selected from the group of molybdenum, molybdenum alloys, tungsten, and tungsten alloys.

BRIEF DESCRIPTION OF THE DRAWINGS

FIGS. 3 and 4 illustrate embodiments incorporating integral femoral ball/stem designs; FIGS. 5, 6, and 7 illustrate embodiments incorporating modular ball designs.

DETAILED DESCRIPTION OF SPECIFIC EMBODIMENTS

Figure 1:
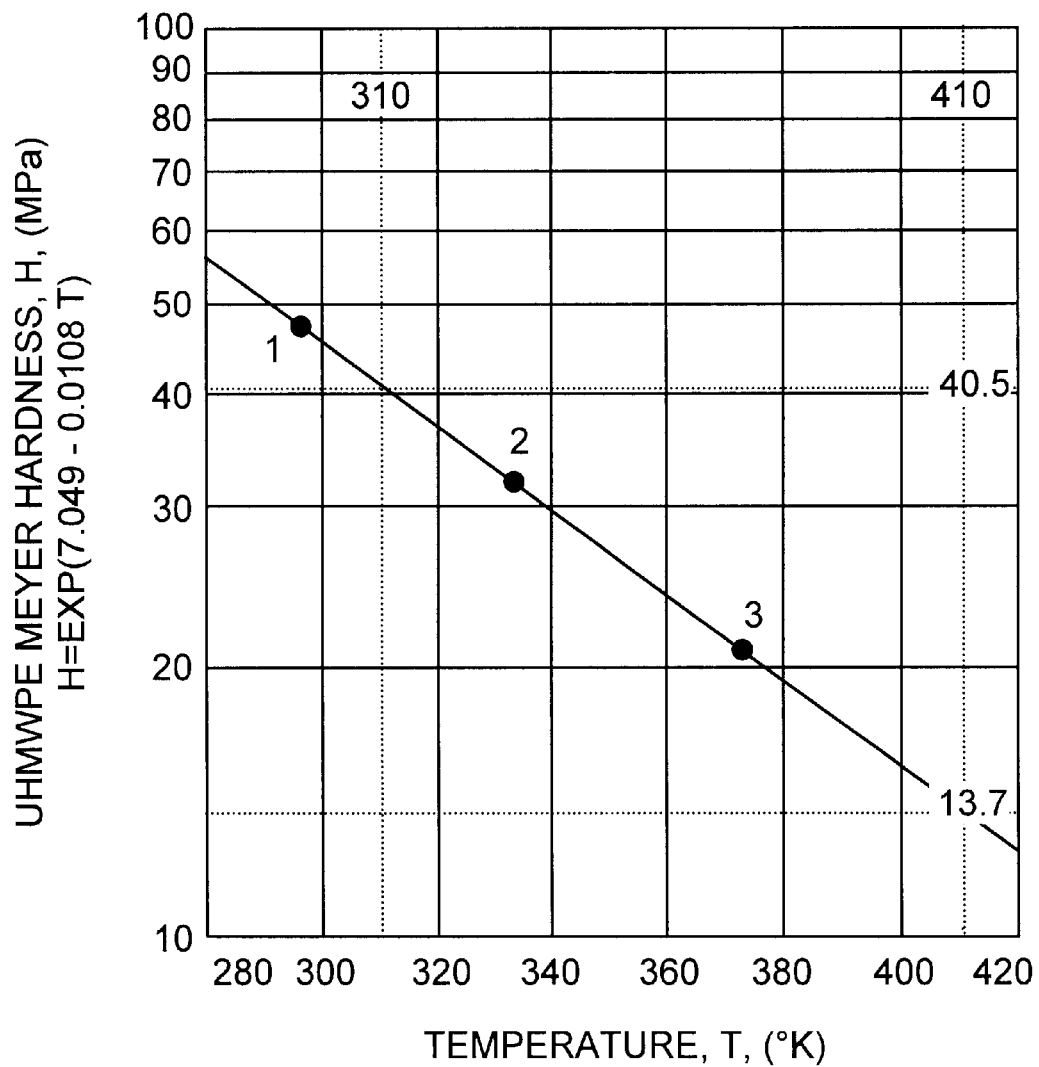
FIG. 1 is a plot of Meyer Indentation Hardness of ultra-high molecular weight polyethylene versus temperature in support of embodiments of the invention.

As a result of the complex thermal paths to the surroundings of an in vivo prosthetic joint and the constraints of the laws of thermal conduction along these paths, the operating temperature at the sliding, load-bearing surfaces are usually above the surroundings temperature. An average sliding surface temperature is governed by the balance or imbalance of the rate of heat generation by friction at regions of frictional contact and the rate of heat conduction away from such regions through the device materials. The level to which this operating temperature rises during use is controlled by the previously described materials and design parameters as well as the use cycle of the device. The parameters of this use cycle include the load on the device, most commonly related to the weight of the user for hip and knee devices, the relative sliding velocity of the joint surfaces which in turn are controlled by device dimensions and cyclic use frequency (in the case of hips and knees the stride or gait rate in strides per unit time), acceleration forces related to increasing the mass velocity of the user, and the overall sliding friction coefficient of the materials pair forming the articulating surfaces of the device, such coefficient modified by body fluids and biological substances present at the surfaces, and finally the time of use. Time of use is a wide ranging variable depending on user activities covering intervals from short transients with intermittent rests, to long steady state uses, typically long walks, and a combination of short and long segments with stops and starts in various innumerable combinations. In the case of artificial hips, the average load at the articulating surfaces depends primarily on body mass. The rate of frictional heat generation depends on the product of load, sliding velocity and friction coefficient as is well known.

The average temperature of the sliding surfaces as a function of time will be governed by transient rises of various durations followed by decays depending on the lengths and sequence of activity segments and rest segments. In the case of prolonged activity of a single type, i.e. walking, a steady state temperature condition may be reached at the sliding surfaces wherein the surface temperatures become nearly constant as frictional heat is conducted into the surrounding 310° K environment though various regions of the device and the thermally connected surrounding biological materials.

Using methods in the literature (Friction and Lubrication of Solids, Part II, Bowden and Tabor, Oxford 1964, pg.217 and Rabinowitz, Friction and Wear of Materials, Wiley 1965, pg.203), estimates, using a simplified model, can be made of the rub temperatures that could be expected under the dynamic conditions of use of an artificial hip constructed of commonly used materials. From Rabinowitz, p. 216, and the known sliding speed of artificial joints (which is most commonly of the order of 0.01–0.1 m/sec), the friction behavior of these joints lies within the boundary lubrication regime. In such a regime, the overall friction coefficient that can be measured experimentally consists of a contribution both from load-supporting regions of direct metal to polymer contact (defined as "breakthrough rub" with its characteristic friction coefficient) and from load-supporting regions where the friction coefficient is that for metal and polymer separated by films. Regions may be defined as small or large load-bearing areas which, in aggregate, support the total load on the sliding surfaces of the device. In vivo, separating films may be synovial fluids, deposits of other natural or biological materials, and their derivatives produced by heat alteration or other chemical reactions caused by the sliding wear process. The weighting law which gives the overall friction coefficient (according to Rabinowitz) is given as:

$$F = a \times F_m + (1-a) \times Fl$$

where:
F is the overall friction coefficient,
a is the fractional area of contact of metal to polymer,
$F_m$ is the friction coefficient measured for direct contact of metal to polymer,
(1−a) is the fractional area of film contact, and
Fl is the friction coefficient of metal to polymer separated by a film.

The apportionment of film areas and direct contact areas depends on factors such as load, surface smoothness and structure, geometry of the opposing sliding surfaces, viscosity of the fluid film, and sliding velocity. These factors are not generally known with precision. It remains that direct contact metal to polymer regions (breakthrough rub) are likely to occur under boundary lubrication conditions and particularly during a period of "start up" motion initiating from rest when fluid films are not established by continuous motion of the articulating surfaces. As shown by Bowden and Tabor, 1950, high rub temperatures will occur at points in sliding systems even in the presence of a flooding fluid film at breakthrough points of this film. This is even more likely to occur in the boundary lubrication regime and result in rub temperatures of the same magnitude as those occurring during rub without lubrication or the presence of surface films. Such "breakthrough rub" temperatures may also occur in small or large regions of frictional contact relative to the total load-support region area and are superimposed upon the average steady state surface temperature of the articulating surfaces of a device. This condition may occur in the case of a long cycle of steady use or a long cycle with short, intermittent stops when fluids film conditions decay and must be reestablished during subsequent start up motion.

In the literature, Bowden and Tabor (1950) teach that at the articulating interface of pairs of sliding surfaces where one of the pair has the property of low thermal conductivity, high "rubbing" temperatures occur at random locations and times. The dimensions of these random event hot spots are small (about $10^{-7}$ m$^2$) and the rise and fall times of the maximum temperatures of these spots are short (about $10^{-3}$ to $10^{-4}$ sec). Depending on the relative thermal conductivities of the materials of the pair, the load, and the sliding velocity, these "rubbing" temperatures may be quite high. In the literature on the friction and wear of prosthetic devices, steady state temperatures have been measured under laboratory conditions at points close to the articulating surface of the ball component of the an artificial hip device. Bowden and Tabor disclose that hot spot rub events usually occur under dry rub conditions but may occur under conditions of flooding film lubrication. In the use of artificial prosthetic devices, dry rub conditions may occur during "start up" motion commencing after a user has paused or rested without motion. During these static load periods, lubricating fluids may be squeezed out of the articulating surface interface load-bearing region. In artificial prosthetic devices, it is expected by analogy with the friction, lubrication, and wear literature that hot spots will occur at sliding interfaces. In the case of a device where one member of the articulating surface pair is a polymer, numerous hot spot temperature rises are expected on the polymer side during a use cycle of any type.

The temperature dependence of the hardness of UHMWPE has been measured under laboratory conditions in support of the art disclosed in this application and are presented in FIG. 1. These hardness measurements at 295°, 333° and 373° K (referenced as items 1, 2, and 3, respectively) show a linear correlation between the natural logarithm of hardness (using the Meyer scale of hardness) and temperature. [Reference points at 310° K and at 410° K are also included in the plot; specifically, an H value of 40.5 MPa at 310° K and an H value of 13.7 MPa at 410° K.] Such a correlation is well known in the art of the behavior of crystalline materials in the commonly defined high temperature region in which use temperatures lie between approximately $0.66 T_{mp}$ ($T_{mp}$ is the absolute melting point of a crystalline material on the Kelvin temperature scale) and $T_{mp}$. For UHMWPE with a nominal melting point of 410° K. and where the mechanical behavior is taken as controlled by the crystalline fraction of the material, the lower bound of this high temperature region is approximately 266° K. The lowest possible operating temperature of UHMWPE in prosthetic devices is 310° K, the baseline environmental temperature, or $0.75 T_{mp}$ placing this UHMWPE in a prosthetic device well within the high temperature operating regime of a crystalline material. With these data in mind, average, transient, and transient superimposed upon average temperature rises will lead to local softening according to the above disclosed hardness-temperature relationship for UHMWPE and, over time and in aggregate, will result in increased wear according to the Holm equation for a device which is not thermally managed. Such thermal management, as described below as embodiments, involves limiting the rise in average and transient sliding surface temperatures in artificial prosthetic devices through the use of biocompatible, high thermal conductivity metals and alloys for construction of the load-bearing component surface (which opposes UHMWPE in present prostheses). It further involves the coupling of these surface regions to heat pipe structures for conduction of frictional heat to distal regions of the device and to the surroundings. To insure that substantially all the frictional heat generated at the sliding load-bearing surface is removed by conduction through the metal side (or side opposing the polymeric surface), the thermal conductivity of the material of this side is selected with a value at least seventy five times greater than the thermal conductivity of the material of the opposing load bearing side. Additionally, reduction of heat flow into UHMWPE may be furthered by microstructural alteration such that the thermal conductivity and diffusivity properties of UHMWPE may be suppressed to values below those same property values for standard UHMWPE material.

Bowden and Tabor (1950) give a simplified model calculation of the surface temperature established between two rubbing solids. This model is used herein to apply to the rub of various materials on UHMWPE under loads and sliding velocities selected as nominal operating conditions for artificial hips. The model is applicable to other prosthetic joints as well; hip joints are modeled as one embodiment.

Two massive surfaces, which are large compared to the area of contact between them and having specific thermal conductivities $k_1$ and $k_2$, touch over a small circular region between them (or junction) of radius a. The total contact area of the load is assumed to be assembled into a single area defined by W/H where W is the load and H is the material hardness. Actually, the load will be subdivided into many points of contact which will reduce each "a" but will, also, proportionately reduce each "W" associated with each "a". As a result of friction at this region, a quantity of heat Q is developed per second and flows away into the two bulk materials. A portion $Q_1$ flows into Body I, taken here to be UHMWPE, and $Q_2$ flows into body II, taken here as the head of a hip prosthesis, and $$Q=Q_1+Q_2$$

It is assumed that a steady state is reached at which the junction temperature attains a steady temperature T, while the bulk of the bodies remain at ambient or surroundings temperature, $T_0$ (body temperature of 310° K). Thermal conductance is defined for the junction by the relation:

Heat flow per second=(thermal conductance)×(temperature drop)

An analogy is invoked by Bowden for the electrical contact case giving the thermal conductance from the junction into body I as $4ak_1$, and that into body II as $4ak_2$. Then $$Q_1=4ak_1(T-T_0)$$

$$Q_2=4ak_2(T-T_0)$$

and $$Q=Q_1+Q_2$$

Hence $$T-T_0=Q/4a(k_1+k_2) \quad (1)$$

With a load W, coefficient of friction u, and the sliding speed v, the rate of heat generation is given by:

$$Q=uWgv/J \quad (2)$$

where J is a conversion factor for mechanical energy to thermal energy units and g is the acceleration of gravity when W is given in mass units.

Substituting (2) into (1) yields:

$$T-T_0=uWgv/4aJ(k_1+k_2) \quad (3)$$

Therefore, as would be expected, the junction temperature T will vary inversely with the thermal conductivity of the ball material, $k_1$, as $k_2$ of UHMWPE (~0.4 W/m° K) is much smaller than $k_1$ for most metals. The rise in surface temperature for hip ball materials is then calculated using the following values:

$T_0$=310° K $u$=0.25 (Range may be from 0.1 to 0.3.)

$W$=2500 Newtons $v$=0.0196 m/sec.—based on a 0.025 m ball, 1 Hz frequency, and 45 deg angular rotation range (10 deg flexion, 35 deg extension).

This is the total length of ball perimeter traversed per second including path retracement. For a 0.032 m ball this value is 0.0252 m/sec., and for a 0.022 mm ball, 0.0173 m/sec. The path is taken as linear.

A lower bound area under load is given, where the contact region is taken as consolidated and round, as the ratio of load to material hardness. The contact area here is based on a load of 2500 N and a Meyer hardness, H, at 295° K of UHMWPE, grade GUR 412, of 46.7 MPa. Thus, the radius, a, of contact is given as:

$$a = (W/\pi H)^{1/2} = 0.00413 \text{ m}$$

$k_2 = 0.41$ W/m° K., thermal conductivity of UHMWPE @ 310° K.

This low value of $k_2$ is disregarded in the calculation of peak rub temperature because it has a negligible effect on the result. The value of $k_2$ is not however inconsequential in the overall problem of wear in prosthetic devices since the thermal conductivity and thermal diffusivity of the UHMWPE determine the extent to which heat flows into a thin, near surface volume (of the UHMWPE articulating surface) under the temperature gradient established by the peak rub temperature governed by $k_1$ and the bulk temperature of the polymer component. Data from the measurement of thermal conductivity of unmodified as well as structure altered UHMWPE is presented below in Table I and clearly indicates that the lower than normal thermal conductivity of structure-altered UHMWPE decreases the rate of heat flow into the UHMWPE side of a device when this material is used. Thermal management by microstructural alteration to reduce $k_2$ below the value for unaltered UHMWPE may be employed to increase device life by maintenance of UHMWPE hardness at a higher level due to lower temperature.

For the purpose of illustration of peak rub temperatures that can be estimated for the stated operating conditions, a range of thermal conductivities of $k_1$ from about 5–125 W/m° K has been selected. This range of thermal conductivities covers several of the conventional materials used for prosthetic devices as well as the improved materials discussed.

Figure 2:
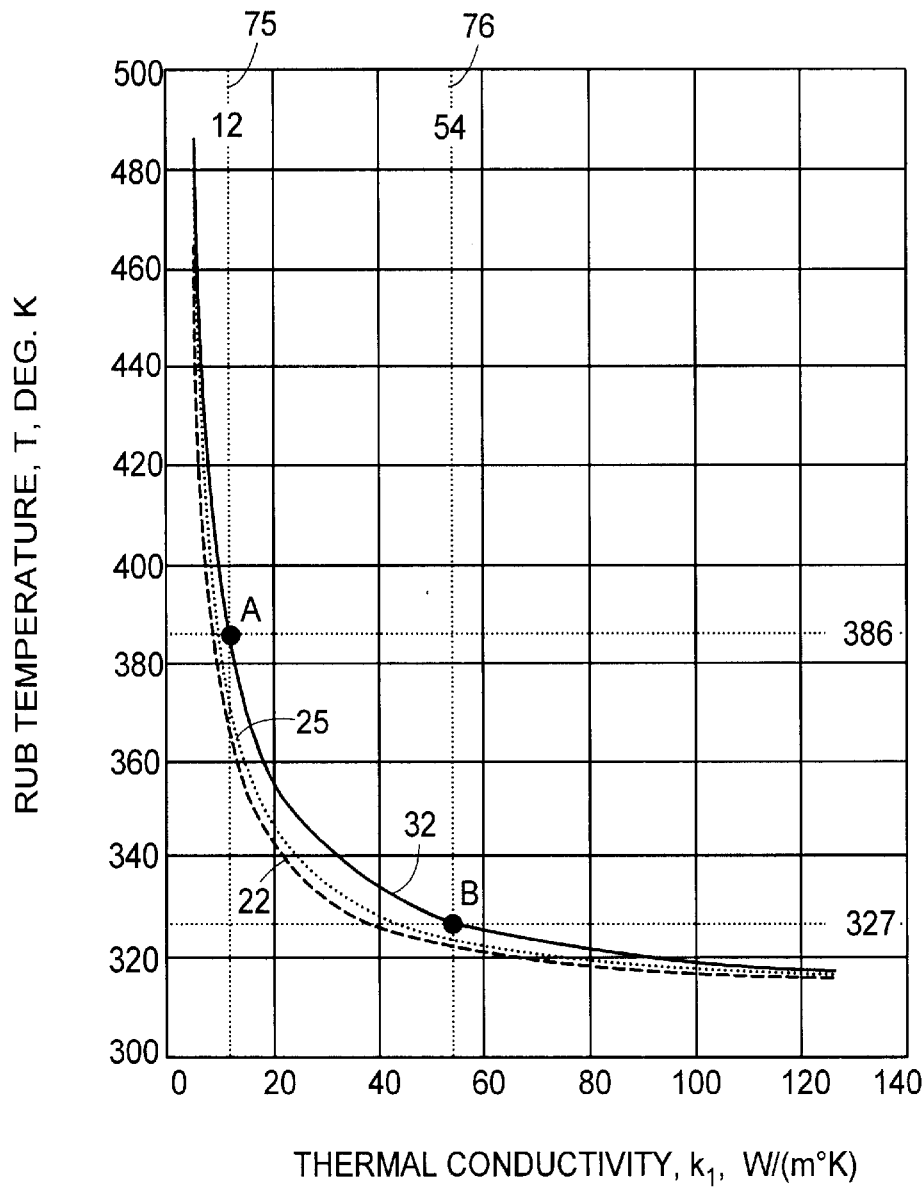
FIG. 2 is a plot of surface rub temperature versus thermal conductivity in support of embodiments of the invention.

Plots of surface temperatures versus $k_1$ are shown as Examples 1,2, and 3 in FIG. 2. Example 1 (ref. 22) represents the temperature when a 22 mm ball is used, Example 2 (ref. 25) represents the temperature with a 25 mm ball, and Example 3 (ref. 32) represents a 32 mm ball. The above calculated temperatures are totals which are comprised of the "rub rise" due to friction added to the surroundings temperature of 310° K. Also shown in FIG. 2 are point A, signifying a calculated temperature of 386° K modeling a 32 mm ball of F-75 alloy [F-75 has a thermal conductivity of about 12 W/m° K (identified as line ref. no. 75), as well as point B signifying a much lower calculated temperature of 327° K modeling a 32 mm ball of a reference gold alloy Au,25%Ag-6%Pt alloy [alloy has a thermal conductivity of about 54 W/m° K (identified as line ref. no. 76)

Values for thermal properties of materials related to this invention are given below in Table I.

TABLE 1

| Material | Thermal Conductivity W/m° K @ 298° K except as noted | Thermal Diffusivity $10^{-7}$ m$^2$/sec |
|---|---|---|
| UHMWPE (reference) | 0.395 @ 310° K | 2.12 @ 310° K |
| UHMWPE (structure modified) | 0.377 @ 310° K | 1.83 @ 310° K |
| Zirconia | 1.67 | |
| Ti6Al4V alloy | 1.72 | |
| Co—Cr—Mo, F-75 type | 12.1 | |
| SS, 304, 316 type | 14.6 | |

TABLE 1-continued

| Material | Thermal Conductivity W/m° K @ 298° K except as noted | Thermal Diffusivity $10^{-7}$ m$^2$/sec |
|---|---|---|
| Alumina | 30.2 | |
| Au, 25% Ag-6% Pt alloy | 54 | |
| Mo, pure (reference) | 138 | |
| W, pure (reference) | 173 | |
| Au, pure (reference) | 318 @ 310° K | 146 @ 310° K |
| Cu, pure (reference) | 401 | |

The structure modified UHMWPE had been gamma irradiated at a 100 MRad dosage and melt stabilized. Standard UHMWPE material was taken from extrusion compacted rod without further processing. Thermal measurements on the UHMWPE were made using a laser flash method that conforms to ASTM E1461-92, "Standard Test Method for Thermal Diffusivity of Solids by the Flash Method. Reference thermal conductivites for pure materials were taken from the 58th Ed. of the Handbook of Chemistry and Physics. Values for Co—Cr—Mo, F-75 type were taken from the AeroSpace Materials Handbook, December 1970 for Stellite 21 alloy. The Au—Ag—Pt data was taken from the ASM Metals Handbook, 1948 Ed. Data for Ti6Al4V and both types of stainless steel were taken from ASM Metals Handbook Desk Ed., 1985. Data for alumina and zirconia were taken from "Oxide Ceramics". Ryshkewitch, Academic Press, 1960.

It is known that all mechanical properties of UHMWPE are temperature dependent over the range of interest for prosthetic devices. Considering that properties of UHMWPE may be controlled by the volume fraction which is purely crystalline material (by analogy with metals and crystalline non-metals) the material operates in these devices case in the "high temperature regime", (i.e. where the operating temperature is $>0.6 T_{mp}$ where T is in ° K. At 310° K. this material is at 0.76 of $T_{mp}$; at 340° K, which is an estimated lower bound rub temperature with materials of the current art, the UHMWPE surface rub temperature may rise to 0.81 $T_{mp}$. As previously disclosed the hardness of UHMWPE is strongly temperature dependent leading to increased wear due to decreased hardness at all points on the surface of a polymer component where such high temperatures, 0.8Tmp, occur.

Adverse system effects which may occur as a result of excessive rub temperatures predicted for Co—Cr—Mo alloy rubbing against UHMWPE under "normal" simulation test conditions as well as "in vivo" include:

1. Local "melting" of UHMWPE with large expansion of small local volumes due to large stepwise density decrease during phase change from crystalline to melt. This could result in an "inverse plowing" effect whereby the local volume rises into the rub plane and gets sheared off by the sliding ball. This effect will occur mostly in crystalline regions. Furthermore the temperature rise predicted from the model, particularly with the F-75 type alloy, will be bounded by the crystalline melting point since heat will be absorbed by the crystalline to melt phase change instead of contributing to further temperature rise on the polymer side.

2. Destruction of heat sensitive organic species indigenous to the local environment either in simulation or in vivo. The residues of this process may produce surface film materials with higher friction coefficients leading to further interface temperature rise and accelerating wear over the rate "normal" for an adhesion or an adhesion+plowing wear model at lower temperature. In addition, asperities in the alloy caused by uneven wearing of carbides versus metal will eventually decrease joint life.

Substantial reduction of rub temperatures in all orthopedic devices installed in patients, including hips, knees, shoulders, and other joints, can be accomplished by use of a high thermal conductivity metal component in conjunction with a UHMWPE mating component. A biocompatible metal system for this purpose can be synthesized using gold as an alloy base and improving its mechanical properties with suitable alloying elements including but not limited to Pt, Pd, Ag, Zn, Cu, Ni and Ir. Such alloys have been conceived and employed in dental applications where non-toxicity, corrosion resistance, wear resistance, strength and toughness are design requirements similar in many regards to those for orthopedic devices. Such alloys have been disclosed in Gold Alloys in Dentistry, by W. S. Crowell, Metals Handbook, ASM 8th Ed. and in, for example, U.S. Pat. No. 4,007,040 to Kropp. It is known that alloying will decrease the thermal conductivity of pure Au to a value below that in its pure form. However, inspection of the data in Table I for existing engineering metals for orthopedic devices shows that even alloyed, an Au base would decrease friction rub temperatures substantially leading to improved wear life of artificial hip, knee and other systems installed in vivo. Use of such Au based material with a thermal conductivity greater than about 54 W/m° K for the first load bearing surface indicates that under the rub temperature conditions used for illustration in FIG. 2, the maximum rise above the baseline 310° K would be about 17° K. For thermal conductivity material where $k_2$ is 90 W/m° K or greater this rise is 10° K or less. Considering that extreme fever in a human may involve a temperature rise of about 4° K these low temperatures in the range of 320 to 327° K define specified low temperature limits and, within the context of this disclosure and appended claims, define "about 310° K" as close to the natural in vivo surroundings temperature at which joints are used.

These same low temperature limits achieved by use of a material with thermal conductivity of 90 W/m° K or greater define an operating temperature rise which allows a second load bearing surface of standard UHMWPE to operate at least 90% of its baseline Meyer hardness of about 40 MPa as indicated in FIG. 2.

A number of device type embodiments, as well as associated materials and processing details derived from the framework presented above, are provided below:

I. An artificial hip prosthetic device in which the ball part of the "standard" ball/cup design is constructed of a gold alloy with a minimum thermal conductivity of 30 W/m° K. This minimum is chosen to bracket and distinguish such material from the response expected from a ball constructed from alumina ceramic.

II. An artificial hip device in which the ball part of the device contains at least 55 atomic % gold alloyed with one or more of Pt, Pd, Ag, Zn, Cu, Ni and Ir.

III. An artificial hip device in which the ball part of the device is composed of at least 55 at % gold and is alloyed with one or more of the above elements to produce an annealed, heat treated, or otherwise processed hardness of at least 120 Vickers hardness number.

IV. An artificial hip device in which the ball part of the device is composed wholly of metallic material described above.

V. An artificial hip device in which the ball part of the device is clad with a gold alloy composed of material described above.

VI. An artificial hip device in which the cladding of the ball with a gold alloy is accomplished by metallurgical bonding by hot isostatic pressing.

VII. An artificial hip device in which the cladding of the ball is accomplished by manufacturing a separate gold alloy piece and attaching such piece to the "stem" of the device with a biocompatible adhesive.

VIII. An artificial hip device in which the ball is manufactured of a gold alloy described above with an integral taper joint for attachment to the main body of the device through the mechanical means of a locking taper.

IX. A high thermal conductivity hip prosthetic device wherein the gold alloy is strengthened by dispersion hardening with a biocompatible nonmetallic phase dispersion.

X. A high thermal conductivity hip prosthetic device wherein the ball is constructed of high thermal conductivity materials other than gold-based, in particular tungsten or molybdenum, or their alloys, using methods of construction described above.

XI. A high thermal conductivity prosthetic device wherein heat transfer away from the articulating surface is augmented by the use of heat pipe structures for promotion of heat flow to distal regions of the device and into the surrounding environment.

XII. The construction of a high thermal conductivity hip prosthetic device wherein the load-bearing cup surface is constructed from the metallic materials described above while the load-bearing ball surface is made from UHMWPE or other biocompatible polymer.

XIII. The use of structure-modified UHMWPE with thermal conductivity and thermal diffusivity of such modified material lower than that of standard unmodified UHMWPE (with values of these parameters given in Table I based on laboratory measurements) for the polymer component of the device in conjunction with any or all of the embodiments briefly described in paragraphs I–XII.

Embodiments of extended life prosthetic hip joints are described below. It should be understood that application to hip joints is illustrative and, in no way limits the use of similar embodiments in other surroundings.

Figure 3:
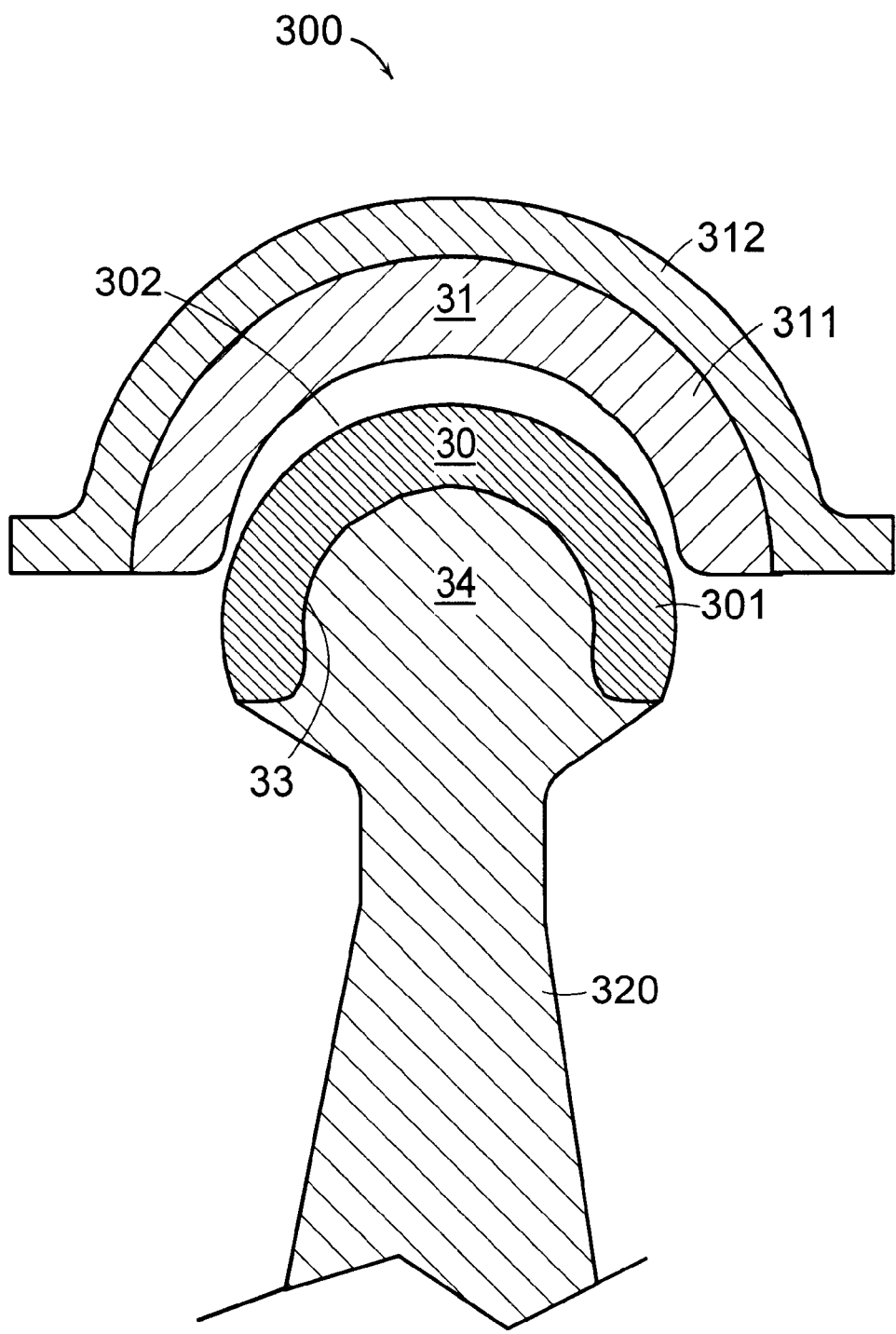
FIGS. 3–7 are cross-sectional views of extended life prosthetic hip joints in accordance with embodiments of the invention.

Regarding a first embodiment with reference to FIG. 3, to dissipate frictional heat generated at the articulating surface of a ball member 30 of an artificial hip 300 mated with an acetabular cup member 31, a layer 301 of gold, gold alloy, or other biocompatible material with thermal conductivity greater than 30 W/m° K is metallurgically bonded to a continuous extension of femoral stem 320 to form a high thermally conductive layer 301 and first load-bearing surface 302. A metallurgical bond is defined as that microscopic structure at the interface of dissimilar materials which is continuous and without voids, maintains the strength of the weaker of the two of the pair, and in the vicinity of the interface has thermal conductivity no less than that of the least thermally conductive material of the dissimilar pair. To afford sliding wear resistance against a relatively soft material (such as UHMWPE), the gold or other selected material may be processed to obtain a material hardness of about 1500 Mpa or greater. The metallurgical bond 33 between layer 301 and stem 320 is created to insure that layer 301 is structurally supported within the device 300 and thermally connected in a way to minimize heat flow resistance at bond 33. In this embodiment, mating acetabular cup member 31 includes a polymeric layer (most usually UHMWPE, in keeping with currently accepted design) configured as first cup member portion 311 which is itself attached and supported by a second cup member portion 312. Materials of construction for portion 312 and the femoral stem 320 are selected from the list of Ti alloys, Co—Cr—Mo alloys, and stainless steel grades 304 and 316 most commonly used for prosthetic devices. These materials are characterized by low thermal conductivity as compared to the high thermal conductivity metals as shown in Table I above. In this embodiment, frictional heat is conducted quickly throughout the region of layer 301 and bond 33 before transmission into the near and distal regions of the femoral ball core (generally 34) and subsequently into the stem 320 and distal regions of the stem before transfer to the surrounding environment. Heat is also conducted from an equatorial region of layer 301 extending below the UHMWPE cup portion 311 that is exposed at rest and during motion directly to the surrounding biological environment.

In a second embodiment, yet still referring to FIG. 3, construction materials are, essentially reversed. In this embodiment, first acetabular cup member portion 311 is made from a material such as gold, gold alloy or other material selected using the same criteria as was used for making layer 301 in the previous embodiment. First acetabular cup member portion 311 is mechanically or metallurgically bonded to the second cup member portion 312. Materials of construction for portion 312 and the femoral stem 320 are, again, selected from the list of Ti alloys, Co—Cr—Mo alloys, and stainless steel grades 304 and 316 most commonly used for prosthetic devices. The relative thicknesses of portions 311 and 312 in the acetabular cup assembly 31 may be varied so that portion 311 is greater and portion 312 is lesser in a way to further increase the heat flux into the supporting biological bone structure of the acetabulum while still insuring adequate mechanical support for mounting devices and loads. In this embodiment, a layer 301 of polymeric material (typically, but not restricted to UHMWPE) is bonded through an engaging surface structure (analogous to bond 33) to the femoral head stem extension or ball core (generally 34) of the femoral stem 320. In this embodiment, frictional heat flow is obstructed in the direction of the stem 320 because of the very low thermal conductivity of polymers when compared to the other metals and alloys of construction. Heat is, instead, directed into an alternate, low resistance thermal path consisting of the acetablular cup 31 and then into the surrounding biological environment, in this case, primarily bone. This low resistance thermal path is an element of this embodiment since it is created through the use of a high thermal conductivity material as well as an expanding heat conduction area, i.e. an increasing heat flow area cross section as the path moves outward toward the periphery of a hemisphere (first cup portion 311). In other embodiments, the heat flow is directed into the core of a hemisphere where the path is constricted by reduction of the cross sectional heat transfer area.

Figure 4:
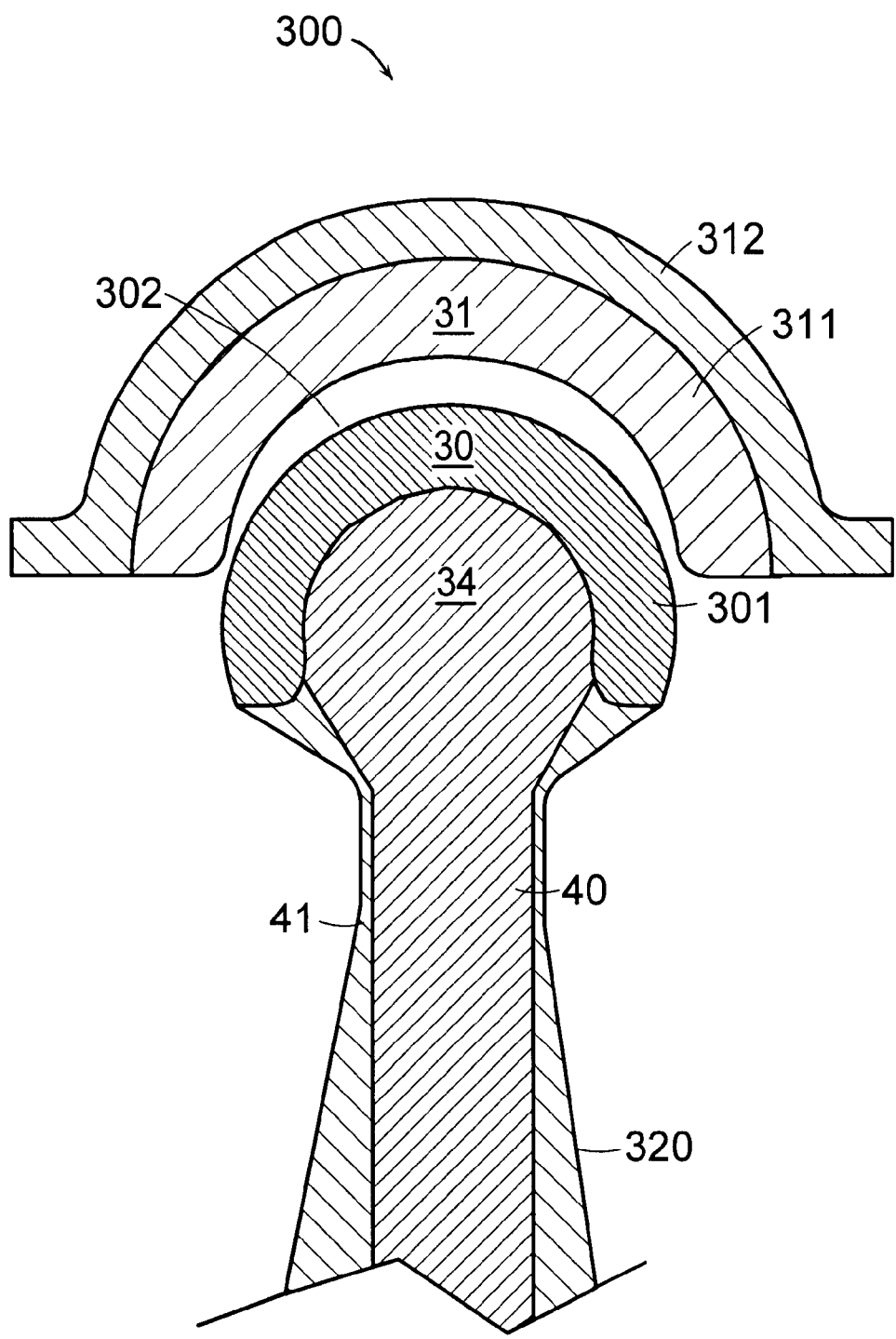

Another embodiment is illustrated as FIG. 4. When compared with the first embodiment with reference to FIG. 3 described above, this embodiment differs in that the device takes further advantage of the coupling of a high thermal conductivity metal as heat pipe member 40 within the core of the femoral stem 320 to a very high thermal conductivity layer 301 on the outer region of the femoral ball core 34. Such a heat pipe member 40 may be constructed from material comprised of, for example, high strength engineering materials such as molybdenum, molybdenum alloys, tungsten, tungsten alloys, high strength copper alloys or other known metals or alloys having both high strength and thermal conductivity. Such materials should have thermal conductivity greater than 30 W/m° K, and, alternatively, greater than 50 W/m° K. Thus, heat pipe member 40 further serves as a load support. Generally, the recommended materials listed for heat pipe member 40 are not biocompatible. In this embodiment, heat pipe member 40 is totally enclosed by layer 301 and by casing 41. Casing 41 may be constructed from the materials used for second cup member portion 312 or other suitably biocompatible material. The use of these materials of construction provides special thermal properties of known heat pipe materials without exposing a device user to metal corrosion products other than those resulting from use of metals of the current art of prosthetic hip joints. To insure maximum strength and minimum thermal resistance at unlike metal interfaces within the device, all regions of the femoral ball member 30 and stem 320 structures (40 and 41) may be metallurgically bonded together using well known metals joining processes such as, for example, hot isostatic pressing.

Figure 5:
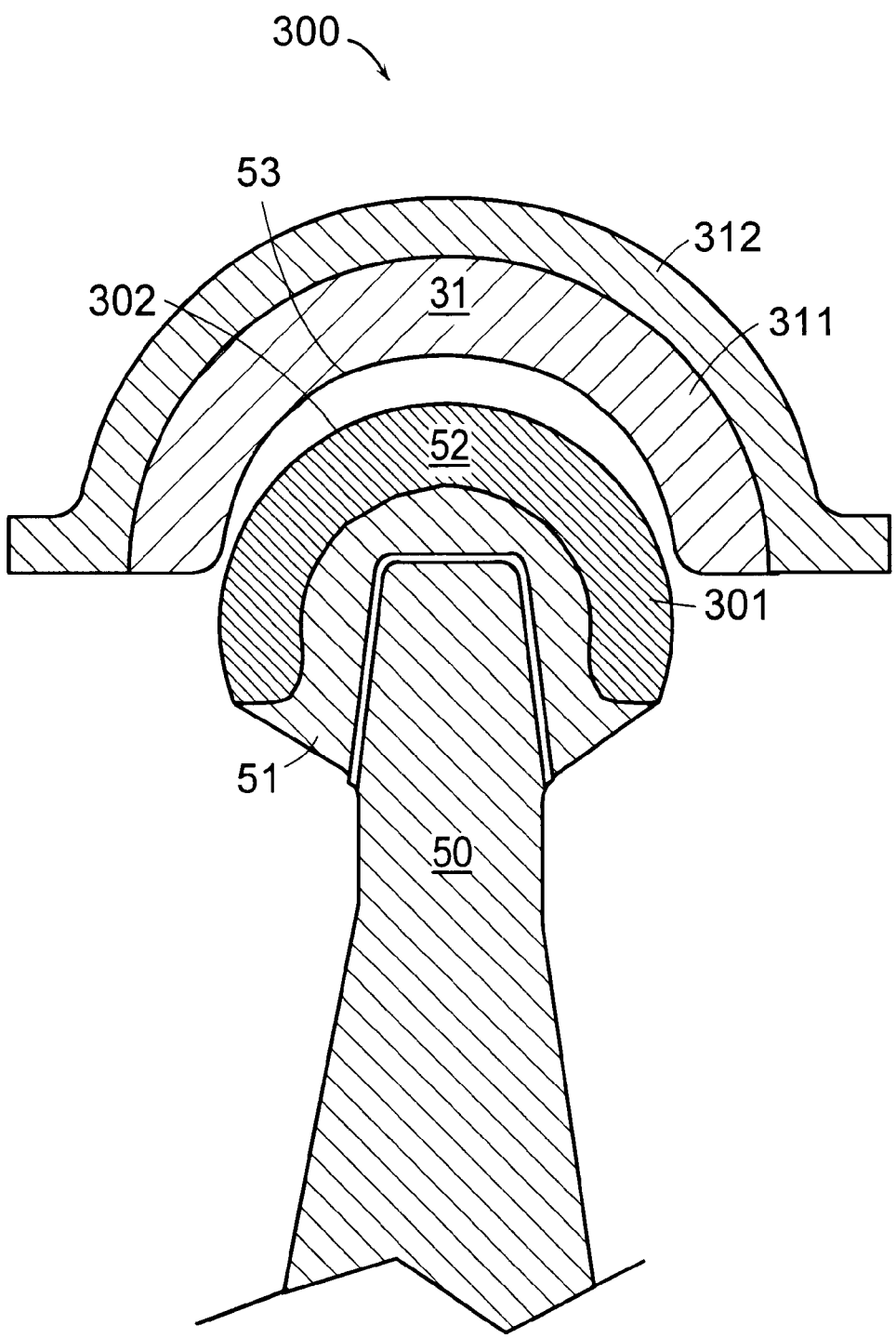

A fourth embodiment of a thermally managed artificial hip is shown in FIG. 5. In this configuration femoral ball 52 is modular and may be attached to the femoral stem 50 using a standard locking taper joint well known in the art. The core region 51 of the modular femoral ball 52 and femoral stem 50 may be constructed of standard prosthetic alloys used in previous embodiments (for example, items 320 and 312). Femoral ball 52 is clad with a layer 301 of high thermal conductivity biocompatible material such as gold, gold alloy, or other material with a thermal conductivity greater than 30 W/m° K as in previous embodiments. This high thermal conductivity alloy comprises the load-bearing surface 302 of the ball 52. Layer 301 is of sufficient thickness to rapidly conduct frictional heat away from the articulating surfaces (first load-bearing surface 302 and surface 53 of first cup portion 311) via an equatorial region of layer 301 extending below the first cup portion 311 that is exposed at rest and during motion directly to the surrounding biological environment as well as through the core of the ball 51 and into the stem 50 of the device.

Referring again to FIG. 5, a fifth embodiment of this invention provides the reversal of material positions in the modular device to conform to those positions described in the second embodiment above. In this embodiment, core region 51 of the modular ball 52 is selected from current prosthetic metals or alloys. Here, polymeric material, most usually UHMWPE is bonded to an engaging surface on the supporting subhemisphere of the ball 52, forming layer 301. What differentiates this embodiment is that, as in the second embodiment (with reference to FIG. 3) described above, the flow path for frictional heat generated at the sliding surface interface 302 is substantially shortened in its distance to the adjoining acetabular bone (distal to second cup member 302) and the thermal resistance of the mechanical taper joint (as well as the low thermal conductivity of the polymer layer 301) do not adversely affect heat flow which is primarily away from these regions. Again, as in the aforementioned embodiment, the ratio of high thermal conductivity material in first cup member 311 can be increased relative to supporting second cup member 312, and incorporated by metallurgical bonding into a monolithic cup structure thereby further enhancing heat flow away from the sliding surfaces.

Figure 6:
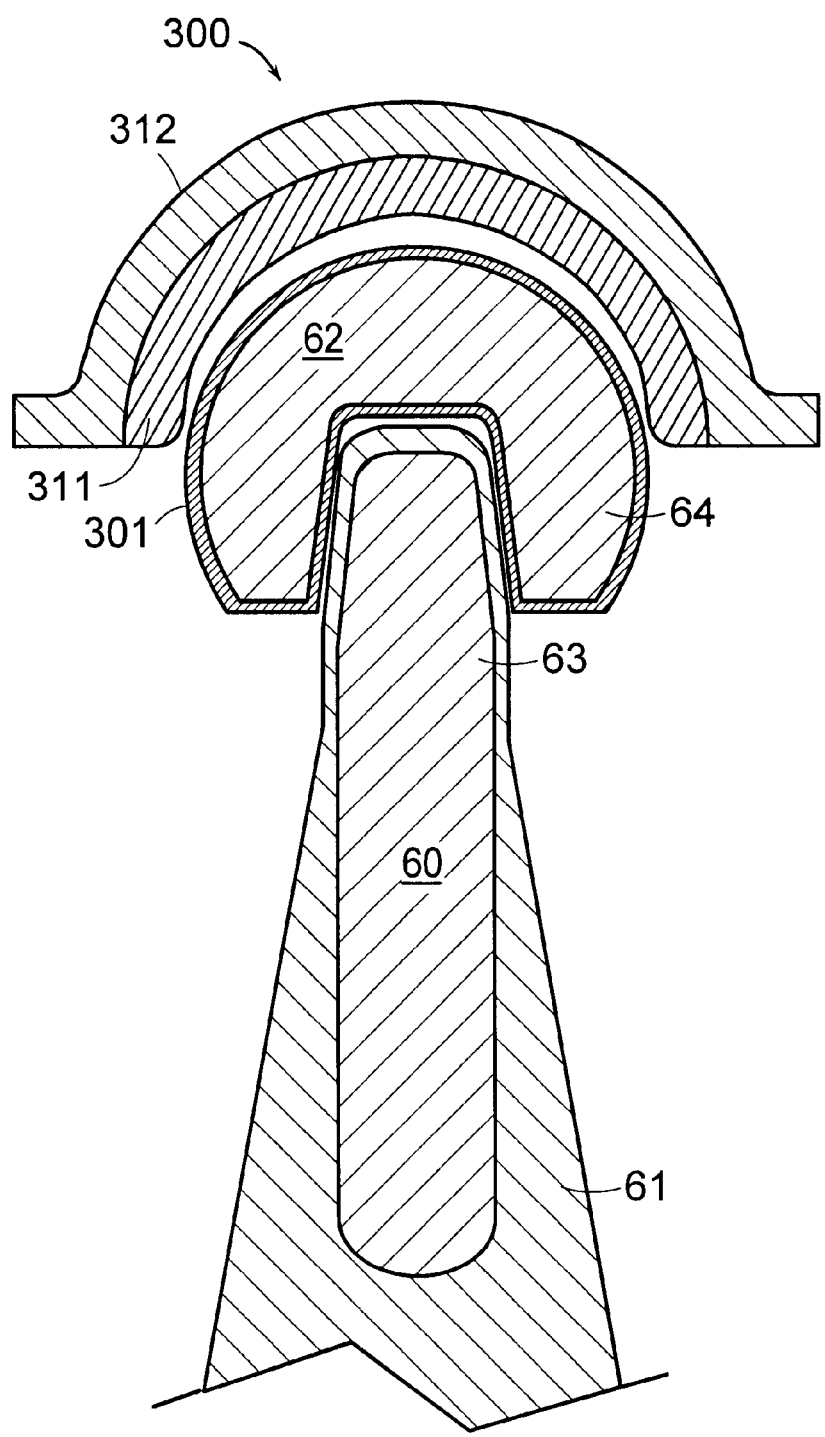

In yet a sixth embodiment of an extended life prosthetic joint through thermal management, FIG. 6 illustrates a cross-sectional view incorporating a heat pipe structure used for both a modular femoral ball head 62 and a stem 60. Standard prosthetic materials previously described may be used to construct second cup member 312, a heat pipe casing 61 and the distal region of the femoral stem. Suitable heat pipe materials of construction may be selected from the group of heat pipe materials identified in the third embodiment having both strength for the load bearing requirements of the device as well as having high thermal conductivity greater than 30 W/m° K, alternatively, greater than 50 W/m°

K. Casing 61 isolates the heat pipe core 63 of the stem 60 from corrosion processes which may occur in the in vivo use surroundings. The heat pipe core 63 of the stem 60 may be metallurgically bonded to casing 61 and the distal region of the femoral stem to insure structural integrity and corrosion resistance. The modular femoral ball head 62 has a ball core 64 of high thermal conductivity heat pipe material (like the material of construction of heat pipe core 63) and a completely surrounding metallurgically bonded surface layer 301 of gold or gold alloy, or other biocompatible material. This alloy should have a thermal conductivity of at least 30 W/m° K. Layer 301 is disposed on all exposed surfaces of ball 62 and is maintained at a thickness sufficient to minimize thermal contact resistance to the stem component of the device as well as to prevent generation of metal ions from the heat pipe material through corrosion processes within the device. In this embodiment, first cup member 311 is a polymer, most usually but not restricted to UHMWPE.

Figure 7:
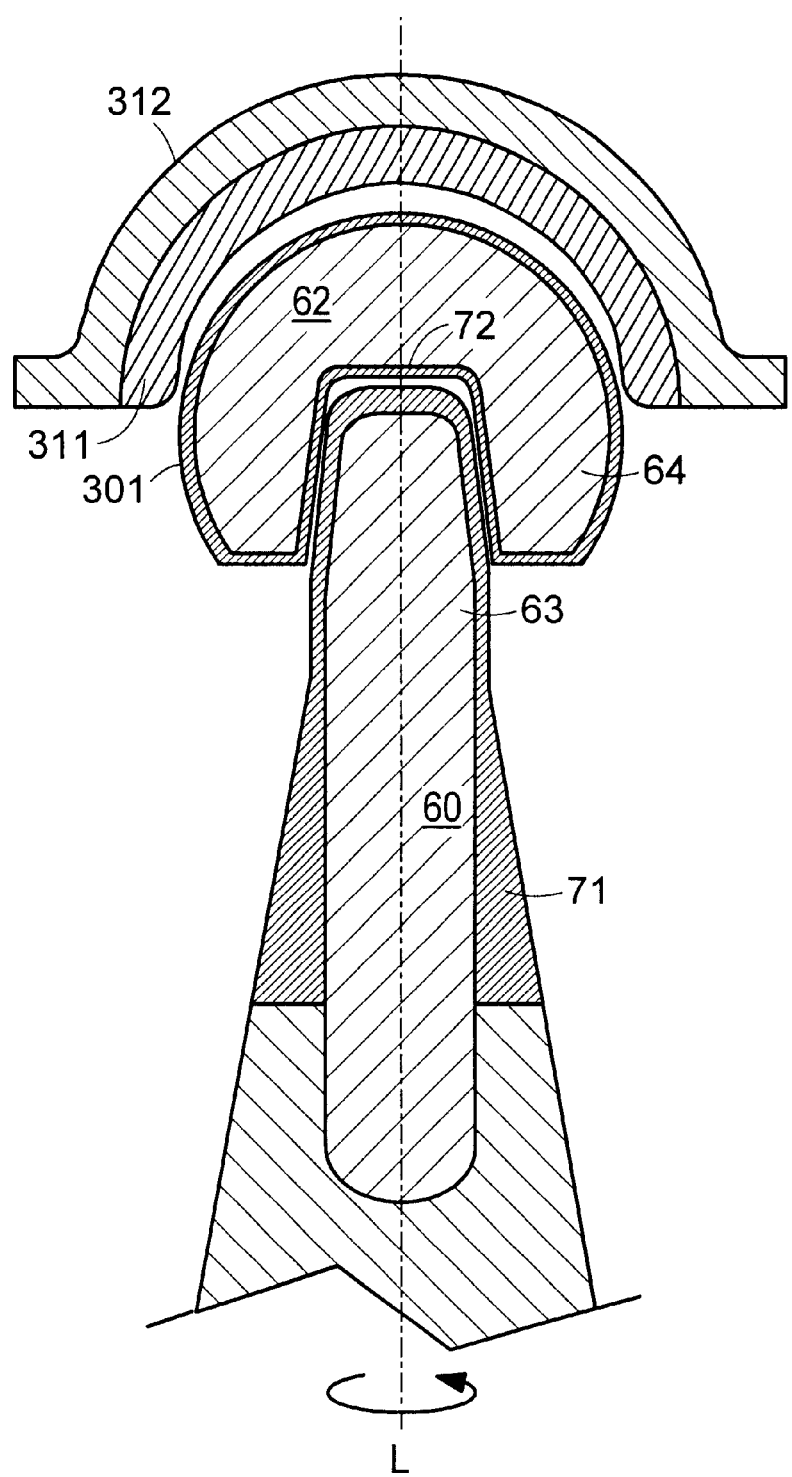

In a seventh embodiment (similar to the sixth embodiment) shown in FIG. 7, the stem 60 region of the device may be clad with gold, gold alloy or other biocompatible material (used for layer 301) with thermal conductivity greater than 30 W/m° K over a section 71 of the stem contiguous with most of the extension of the heat pipe core 63 into the stem along axis L . This embodiment of a prosthetic joint maximizes heat transfer by conduction from within the stem 60 to the surrounding environment. This cladding over section 71, as well as additional clad area 72 acts to further reduce the thermal contact resistance at the taper joint within the modular ball. The coating in this area acts to further improve the device by reducing the total exposed area constructed from standard prosthetic materials and decreasing the amount of metal ion corrosion products which may be produced from such materials.

Although the embodiments described have used artificial hip devices for purposes of illustration, it would be clear to anyone skilled in the art that extended life improvements through thermal management as taught in this in invention could be achieved for other design variations of the hip device as well as a full range of artificial knee devices which are heavily loaded and also subject to frictional heating and wear of the softer material of the sliding pair, most usually UHMWPE in the current art.

For knees and other high stress prosthetic devices the principle of high thermal conductivity cladding of the metal side of knee device would be applied and further heat transfer augmentation could be achieved through the use of clad heat pipe construction.

Although the invention has been described with reference to several embodiments, it will be understood by one of ordinary skill in the art that various modifications can be made and extension to other types of prosthetic devices can be made without departing from the spirit and the scope of the invention, as set forth in the claims.

What is claimed is:

1. A prosthetic joint comprising:
   a first member comprising ultra-high molecular weight polyethylene, having a first load-bearing surface; and
   a second member comprising:
      a second body portion; and
      a second load-bearing portion, having a second load-bearing surface, the second load-bearing portion comprising a metallic material having a thermal conductivity greater than about seventy-five times the thermal conductivity of ultra-high molecular weight polyethylene, the thermal conductivity measured at about 310° K, the second load-bearing portion clad onto the second body portion;
   the surfaces slidingly disposed relative to each other; the surfaces, when loaded, defining a region of frictional contact where heat is generated;
   wherein the joint is configured to thermally manage the region of frictional contact by heat conduction through the second member.

2. A prosthetic joint according to claim 1 wherein the thermal conductivity of the second member is greater than about 30 W/m° K.

3. A prosthetic joint according to claim 1 wherein the second body portion is made from different material than is the second load-bearing portion.

4. A prosthetic joint according to claim 1, wherein the prosthetic joint is capable of serving as an artificial hip.

5. A prosthetic joint according to claim 4, wherein the first member is ball shaped and the second load-bearing surface is cup-shaped and is sized to mate with the first member.

6. A prosthetic joint according to claim 4, wherein the second member is ball-shaped and the first load-bearing surface is cup-shaped and is sized to mate with the second member.

7. A prosthetic joint according to claim 1, wherein the prosthetic joint is capable of serving as an artificial knee.

8. A prosthetic joint according to claim 1, wherein the second load-bearing portion contains gold.

9. A prosthetic joint according to claim 8, wherein the second load-bearing portion contains a gold alloy having at least 55 atomic percent gold.

10. A prosthetic joint according to claim 1, wherein the second member is made from material selected from the group consisting of gold, gold alloys, molybdenum, molybdenum alloys, tungsten, tungsten alloys, copper and copper alloys.

11. A prosthetic joint according to claim 10, wherein the material is a gold alloy.

* * * * *